United States Patent [19]

Crounse et al.

[11] Patent Number: 4,647,578

[45] Date of Patent: Mar. 3, 1987

[54] PHOTOTOXIC INSECTICIDAL COMPOSITIONS AND METHOD OF USE THEREOF

[75] Inventors: Nathan N. Crounse, Myrtle Beach, S.C.; James R. Heitz, Starkville, Miss.

[73] Assignee: Sterling Drug Inc., New York, N.Y.

[21] Appl. No.: 584,833

[22] Filed: Feb. 29, 1984

Related U.S. Application Data

[63] Continuation-in-part of Ser. No. 557,507, Dec. 1, 1983, abandoned.

[51] Int. Cl.[4] ................ A01N 43/00; A01N 43/16
[52] U.S. Cl. ................................ 514/454; 514/191
[58] Field of Search ............... 424/283; 514/454, 191

[56] References Cited

U.S. PATENT DOCUMENTS

| | | | |
|---|---|---|---|
| 3,001,908 | 9/1961 | Harrison | 424/283 |
| 3,873,576 | 3/1975 | Petrzilka | 424/283 |
| 4,320,140 | 3/1982 | Crounse et al. | 424/283 |
| 4,474,751 | 10/1984 | Haslam et al. | 424/283 |

FOREIGN PATENT DOCUMENTS

| | | | |
|---|---|---|---|
| 49-35145 | 9/1974 | Japan | 424/283 |
| 51-88643 | 8/1976 | Japan | 424/283 |

OTHER PUBLICATIONS

Heitz and Wilson, Photodegradation of Halogenated Xanthene Dyes, ACS Symposium Series, No. 73, Disposal and Decontamination of Pesticides, 1978.

Dr. Antonio Barbieri, Fluorescent Sensitizers as Larvicides, Photodynamic Action of Light (1928), AQ VII, 456–463.

Hans Schildmacher, Biol. Zentr., 69, 468–477 (1950), Concerning Photosensitization of Mosquito Larvae with Fluorescent Dyes.

Gajanan D. Pimprikar, Bev. R. Norment and James R. Heitz, Environmental Entomology, 8 (5), 855–859 (1979).

Yoho, Butler and Weaver, J. Econ., 64, 972–973 (1971), Photodynamic Effect of Light on Dye-Fed House Flies.

Primprikar, Fondren and Heitz, Environmental Entomology, 9 (1), 53–58 (1980).

Fondren and Heitz, Environmental Entomology, 7 (6), 843–846 (1978).

Broome, Callaham and Heitz, Environmental Entomology, 4 (6), 883–887 (1975).

David and Heitz, Agricultural and Food Chemistry, 26, (1), 99–101, 1978.

*Primary Examiner*—Allen J. Robinson
*Attorney, Agent, or Firm*—William G. Webb; B. Woodrow Wyatt; Paul E. Dupont

[57] ABSTRACT

Water insoluble, photodynamic insecticidal compositions comprising the free acids of erythrosin B, phloxin B, rose bengal, octabromofluorescein or fluorescein or the aluminum lakes thereof, optionally including a dispersant, aqueous dispersions of the same and a method of combatting adult insects and insect larvae by use of the same.

23 Claims, No Drawings

PHOTOTOXIC INSECTICIDAL COMPOSITIONS AND METHOD OF USE THEREOF

RELATED APPLICATIONS

This is a continuation-in-part of our prior copending application Ser. No. 557,507, filed Dec. 1, 1983 now abandoned.

BACKGROUND OF THE INVENTION (a) Field of the Invention

This invention relates to insecticidal compositions containing phototoxically effective ingredients and to the method of use thereof.

(b) Information Disclosure Statement

The use of sodium salts of various xanthene dyes as insecticides is well known. Such dyes owe their insecticidal effect to a photodynamic action of visible light on adult insects of their larvae that have ingested the dyes, for example from aqueous solutions thereof. A suggested mechanism for the toxic effect requires that the dye, in a ground singlet state, first absorbs a photon of visible light and thus becomes excited to a higher singlet energy state. Of several different possible paths the excited dye molecule can then take, in one path, it can transfer its excess energy to another molecule, such as an oxygen molecule, to form a highly reactive and toxic singlet oxygen. The toxic effect exerted by the thus energized oxygen is then manifested by tissue damage in the insects or larvae of such nature as to cause death of the organisms. [Heitz and Wilson, Photodegradation of Halogenated Xanthene Dyes, ACS Symposium Series, No. 73, Disposal and Decontamination of Pesticides, 1978]. This mechanism requires that the molecule be phosphorescent, and the greater the phosphorescence of the dye, the greater its photodynamic toxicity should be.

This mechanism also requires, of course, that the dye be ingested by the adult insects or their larvae, and in virtually all approaches to date to the use of xanthene dyes as photodynamic insecticides, water soluble forms, for example the sodium or potassium salts, are dissolved either in water, for example to test the efficacy of the dyes against mosquito larvae, or in sugar solutions, for example to serve as feed bait in studies against fire ants.

Thus Barbieri, Rivista di Malariologie, AO VII, 456–463 (1928) tested a variety of fluorescent materials for phototoxicity and found that rose bengal in combination with erythrosin as a "sensitizer" was particularly effective against Anopheles spp. Also found to be effective were erythrosin/esculin and erythrosin/eosin combinations, while an acridine/esculin combination was ineffective. Rose bengal alone, at dilutions from 1:10,000 to 1:2,000,000, was also effective, but esculin, acridine, sulfonal and Magdala Red (phloxin B) alone were all found to be ineffective.

Schildmacher, Biol. Zentr., 69, 468–477 (1950) examined a series of fluorescent dyes (uranin A, erythrosin J, eosin H.8.G., rose bengal, phloxin B., rhodamine B, acridine red and tryptaflavin) for their photodynamic toxicity to *Anopheles maculipennis* (second and third instars), *Anopheles superpictas* and *Aedes aegypti* mosquito larvae. Rose bengal and acridine red were found to be the most effective in all experiments at dilutions up to 1:100,000, and erythrosin and phloxin B were also found to be effective. Uranin, erythrosin and rhodamine were found to be ineffective.

Pimprikar, Norment and Heitz, Environmental Entomology, 8 (5), 855–859 (1979) studied the photodynamic toxicity of rose bengal against the mosquito larvae, *Culex pipiens quinquefasciatus* and *Aedes triseratus*, and found it to be an effective insecticide.

Yoho, Butler and Weaver, J. Econ. Ent., 64, 972–973 (1971) studied the photodynamic toxic effect of rhodamine, rose bengal, erythrosin B, eosin blue, phenosafranin, methylene blue chloride and uranine against house flies. Rhodamine, rose bengal and erythrosin B were found to be quite effective, and eosin blue moderately so. Phenosafranin, methylene blue chloride and uranine were found to be largely ineffective.

Pimprikar, Fondren and Heitz, Environmental Entomology, 9 (1), 53–58 (1980), tested erythrosin B against house fly larvae, *Musca domestica*, in chicken manure and found it to be an effective insecticide.

Fondren and Heitz, Environmental Entomology, 7 (6), 843–846 (1978) found rose bengal, erythrosin B, phloxin B, eosin Y and tetrachlorofluorescein to be photodynamically toxic in varying degrees against face flies, *Musca autumnalis*. Fluorescein, however, produced no toxic response.

Broome, Callaham and Heitz, Environmental Entomology, 4 (6), 883–886 (1975) found phloxin B and rose bengal to be effective insecticides against black imported fire ants, *Solenopsis richteri*, whereas erythrosin, eosin Y and rhodamine B were found to be ineffective.

David and Heitz, Agricultural and Food Chemistry, 26 (1), 99–101 (1978) describe the use of phloxin B free acid (D and C Red 27) in bait for fire ants, *Solenopsis richteri* and *Solenopsis invicta*. The bait consisted of corn cob grits, soybean oil and phloxin B free acid. The latter form of the dye was used, because it is soluble in the soybean oil, whereas the sodium salt (D and C Red 28) is not. The bait toxicity was found to be light dependent as well as light independent. The light dependent action is effective in hours, while the light independent action is effective in days.

Crounse and Heitz, U.S. Pat. No. 4,320,140 disclose synergistic insecticidal compositions containing at least one insecticidally active water-soluble xanthene dye selected from erythrosin and rose bengal in admixture with the essentially non-insecticidally active and synergistically-effective fluorescein sodium.

SUMMARY OF THE INVENTION

We have surprisingly found that aqueous suspensions of certain water insoluble xanthene dye free acids or their aluminum lakes, either alone or in combination with one another, have photodynamic insecticidal activity superior to their corresponding water soluble sodium salt forms, whether viewed from the perspective of the lethal concentration effective to produce fifty percent mortality (i.e. the $LC_{50}$) or from the perspective of a more rapid kill time (the Lethal Time$_{50}$, i.e. the $Lt_{50}$).

It has also been found that the superior insecticidal activity of the subject xanthene dye free acids and their aluminum lakes can be further augmented by combining the free acids or the lakes, either alone or in combination with one another, with dispersants.

Accordingly, in one aspect, this invention provides a method for combatting adult insects and insect larvae comprising causing the insects or larvae to ingest compositions containing said xanthene free acids or their aluminum lakes, whereby the adult insects or insect larvae die upon thereafter being exposed to visible light.

In another aspect, the invention provides a method for combatting adult insects and insect larvae comprising treating an environment in which such insects live or breed with said compositions.

In another aspect, the invention provides insecticidal compositions containing one or more of said xanthene free acids or their aluminum lakes in combination with a dispersant.

DETAILED DESCRIPTION OF THE PREFERRED EMBODIMENTS

More specifically, we have found that aqueous suspensions of certain water insoluble xanthene dyes or their aluminum lakes, either alone or in combination with one another, have photodynamic insecticidal activity and, in fact, quite surprisingly they have greater insecticidal activity than aqueous solutions of the corresponding water soluble sodium salts.

The dyes, of the xanthene class which we have found to possess such superior insecticidal activity, and which are the subject of this invention, are the aluminum lake and free acid forms of erythrosin B (2',4',5',7'-tetraiodofluorescein), having the formula:

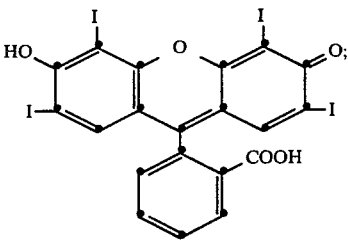

phloxin B (2',4',5',7'-tetrabromo-3,4,5,6-tetrachlorofluorescein), having the formula:

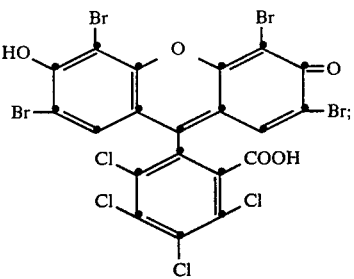

rose bengal (2',4',5',7'-tetraiodo-3,4,5,6-tetrachlorofluorescein) having the formula:

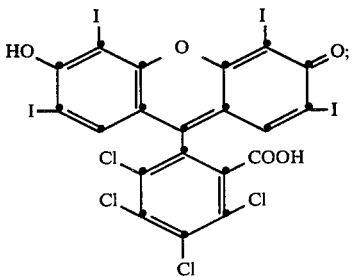

octabromofluorescein (2',4',5',7',3,4,5,6-octabromofluorescein) having the formula:

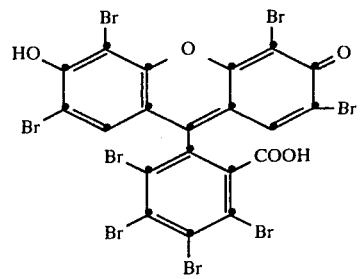

and fluorescein, having the formula:

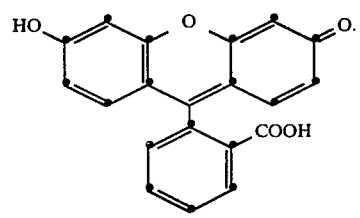

Hereinafter, for the sake of brevity, these xanthene dye free acids (F.A.) will be identified as erythrosin B F.A., phloxin B F.A., rose bengal F.A., octabromofluorescein F.A. and fluorescein F.A.

As stated before, the above-identified free acids or their aluminum lakes, either alone or in combination with one another, show superior photodynamic insecticidal activity, as determined against mosquito larvae, *Culex pipiens quinquefasciatus*, relative to their corresponding water soluble disodium salts. This finding is surprising, not only because one would expect the water soluble forms, which would be more readily available for ingestion by the organisms, to be more toxic than the water insoluble free acids, it is all the more surprising, in the case of fluorescein, F.A., because neither the sodium salt nor the free acid forms thereof had heretofore been known to possess any significant insecticidal activity.

Many insecticides useful for insect control present ecological problems in use, because conventional insecticides are not only indiscriminate in their action, they are, in addition, often stable to biological degradation and thus can have long lasting toxic effects in nature. Moreover, many conventional insecticides are not only toxic to insect life, they are also toxic to man, and thus great care must be exercised with such insecticides to insure that they not be introduced into the food chain of man and domestic animals. An ideal insecticide thus is one which is not only selectively toxic to insects but which is also readily biodegraded.

As stated above, certain water soluble sodium or potassium salts of xanthene dyes, such as erythrosin B, phloxin B and rose bengal, have long been known to have photodynamic insecticidal activity. These compounds have utility in foodstuffs and in certain pharmaceutical applications. They are thus known to be essentially non-toxic to mammals and to be safe for human consumption or human treatment. These xanthene dyes are also known to be readily photodegradable in visible light, and thus they are ideal insecticides.

The free acid forms of these dyes are similarly non-toxic, are also readily photodegradable and thus, like the sodium or potassium salts, would be ideal insecticides. The free acids, however, possess the further advantage over the soluble salts in that, being more toxic to insects as we have discovered, smaller amounts of the free acids are required to achieve the desired insecticidal control effect, and they are thus more economical to use.

It has also been found that the superior insecticidal activity of the subject xanthene free acids can be further augmented by combining the free acids or their aluminum lakes, either alone or in combination with one another, with dispersants.

The solid forms of the free acids are prepared by precipitation from their aqueous alkaline salt solutions by the slow addition of the latter to an excess of mineral acid. Chemical blends of different free acids can be prepared in similar manner by co-precipitation of two or more of the acids from their alkaline solutions.

Alternatively, physical blends of different free acids in dry powdered form can be prepared by physical blending of the separate free acid or aluminum lake components with a ribbon blender, a ball mill or a V-shell blender.

The aluminum lakes used in the practice of the invention are commercially available.

The dry powdered compositions of the free acids or their lakes, in combination with a dispersant, are advantageously prepared by spray drying a dispersion of the acid or the lake in water having the desired dispersant dissolved therein.

In combatting adult insects or insect larvae, the compositions of the invention are spread, either in the form of their aqueous dispersions or in their finely divided powder form, on areas where the insects live or breed, for example in barnyard or poultry farm areas for combatting flies. In combatting aquatic insects or larvae, such as mosquitoes, the compositions of the invention, either in the form of their aqueous dispersions or in their finely divided powder form, are added to the bodies of water in which the insects breed. The amounts of the aqueous dispersion forms of the compositions or of the dried powder forms to be used in a particular application can be calculated from toxicity data, determined experimentally. In the case of use of the compositions to combat aquatic insects, the amounts of the compositions to be used are readily calculated from the $LC_{50}$ values determined experimentally, as will be described below, and the estimated volume of the water to be treated.

The following examples illustrate various insecticidal compositions of the invention and their efficacy.

EXPERIMENTAL PROCEDURE

In each of the experiments described below in which water soluble sodium salt forms of the test dyes were used, the following standard test procedure was followed: A standard stock solution of the dye composition containing one part dye per thousand parts of water (based on pure color, P.C., of the dye) was prepared by dissolving sufficient dye in deionized water to provide 0.1 g. of pure dye per 100 ml. of solution. Serial dilutions of the stock solution were then made by pipetting appropriate aliquots from the stock solution into 300 ml. capacity transparent plastic dishes containing 10 fourth instar larvae of *Culex pipiens quinquefasciatus* Say in sufficient deionized water to provide a total volume in each cup of 100 ml. after addition of the aliquot. Five such cups for each dilution were prepared so that a total of 50 larvae were used for each dilution.

In cases where water insoluble free acid or aluminum lake forms of the dyes were used, sufficient amounts of individual samples of the dry powdered dye compositions were weighed out onto aluminum foil sheets so as to provide the desired concentration of the dye (based on P.C.) in each 100 ml. of deionized water. The dry powders were then dropped onto the surface of the water in each cup containing 10 larvae each, and the foil was gently tapped to remove the dye sample. As in the case of the water soluble salt forms, 5 cups, each containing 10 larvae, were used for each concentration of dye composition. In every experiment, 5 cups containing only deionized water and 10 larvae per cup were used as a control. Since no mortalities were observed in any of the control samples, the totally negative results of such control experiments have been omitted from the tables which follow.

The dishes containing the larvae were then exposed to light provided by pairs of 40 watt General Electric cool white fluorescent bulbs in light fixtures adjusted to a height approximately 8 cm. above the cups which produced a photometer-measured intensity of light at the surface of the test mixtures of 1200 $\mu E/m^2 \cdot sec$. The cups were then monitored for mortality at 0.25, 0.5, 0.75, 1.0, 1.5, 2, 3, 4, 5, 6, 7 and 24 hours after commencement of illumination. The criterion for larval mortality was taken to be the failure of the larvae to respond when probed.

The total number of dead larvae in each treatment were tabulated, and from these tabulations the $LC_{50}$, the lethal concentration (in ppm) necessary to kill fifty percent of the treated larvae and the $LT_{50}$, the length of time of light exposure (in hours) effective to kill fifty percent of the treated larvae, were calculated by probit analysis using the method described by Finney, D.J., Probit Analysis, Third Edition, Cambridge University Press, Cambridge.

With the exception of the tests to be described below using octabromo-fluorescein sodium salt, octabromo-fluorescein free acid without added dispersant and octabromofluorescein with sodium lauryl sulfate (SLS) as added dispersant, all experiments were duplicated by a second, independent experimentalist. In the case of octabromofluorescein sodium salt and octabromofluorescein with SLS as added dispersant, one set of experiments was run in which a total of 50 larvae at each concentration were used. In the case of the free acid without added SLS, a total of 50 larvae were used at each of the 0.25, 0.5, 24 and 48 ppm concentrations, while a total of 100 larvae were used at each of the 0.75, 1, 2, 4, 8 and 12 ppm concentrations.

EXPERIMENT 1

In this experiment, the insecticidal activities of the xanthene dye sodium salts and their corresponding free acids were determined. Test samples of each of the sodium salts of erythrosin B, phloxin B, rose bengal, octabromofluorescein and fluorescein and their corresponding free acids were prepared by subjecting samples of each to dispersion in tap water with an Eppenbach Homo-Mixer for periods from thirty to forty minutes and then spray drying the resulting solutions or dispersions.

The results, obtained in the toxicity test procedure against Culex larvae described above, are given in Table Ia and Table Ib below. (Here, and in the other tables which follow, results of the two separate experiments are given on separate lines for each of the compositions.)

hour at 8 ppm) in comparison with the sodium salt. The results obtained in the second experiment gave insuffi-

TABLE Ia

| Compound | $LC_{50}$ (ppm)/Time (Hours) | | | | | | | | | | | |
|---|---|---|---|---|---|---|---|---|---|---|---|---|
| | 0.25 | 0.5 | 0.75 | 1.0 | 1.5 | 2 | 3 | 4 | 5 | 6 | 7 | 24 |
| erythrosin B Na+ | x | x | x | x | x | x | x | x | x | x | x | 21.0 |
| | x | x | x | x | x | x | x | x | x | x | x | 22.6 |
| erythrosin B | x | x | x | x | x | x | x | x | x | x | 3.5 | 1.1 |
| free acid | x | x | 39.4 | 19.1 | 19.9 | 14.2 | 7.9 | 6.8 | 6.4 | 6.0 | 5.7 | 3.3 |
| phloxin B Na+ | x | x | x | x | x | x | x | x | x | x | x | 17.1 |
| | x | x | x | x | x | x | x | x | x | x | x | 13.4 |
| phloxin B | x | x | x | x | x | x | x | x | x | x | x | 14.2 |
| free acid | x | x | x | x | x | x | x | x | x | x | x | 24.8 |
| rose bengal Na+ | x | x | x | x | x | x | x | x | x | x | x | 14.7 |
| | x | x | x | x | x | x | x | x | x | 179.3 | 16.28 | 15.4 |
| rose bengal | x | 23.1 | 6.8 | 4.8 | 3.2 | 3.0 | 2.7 | 2.3 | 2.2 | 2.1 | 2.0 | 1.9 |
| free acid | x | x | x | x | x | x | x | x | x | x | x | x |
| octabromofluorescein Na+ | x | x | x | x | x | x | x | x | x | x | x | 66.2 |
| | * | * | * | * | * | * | * | * | * | * | * | * |
| octabromofluorescein free acid | * | x | x | 34.1 | 27.0 | 22.9 | 16.8 | 13.5 | 10.0 | 9.0 | 6.7 | 2.6 |
| | * | * | * | * | * | * | * | * | * | * | * | * |
| fluorescein Na+ | x | x | x | x | x | x | x | x | x | x | x | x |
| | x | x | x | x | x | x | x | x | x | x | x | x |
| fluorescein | x | x | x | x | x | x | x | x | x | x | 29.9 | 8.4 |
| free acid | x | x | x | x | x | x | x | x | x | x | x | 10.2 | x Here and elsewhere in this specification, this indicates that there was an insignificant regression of the data to permit calculation of the $LC_{50}$ or $LT_{50}$ values because of insufficient toxicity.
* Here and elsewhere in this specification, this indicates that compositions were not tested at the indicated time or concentration.

TABLE Ib

| Compound | $LT_{50}$ (Hours)/Concn. (ppm) | | | | | | | | | | | |
|---|---|---|---|---|---|---|---|---|---|---|---|---|
| | .25 | .5 | .75 | 1 | 2 | 4 | 8 | 12 | 24 | 48 | 96 | 192 |
| erythrosin B Na+ | * | * | * | * | x | x | x | x | x | x | x | x |
| | * | * | * | * | x | x | x | x | x | x | x | x |
| erythrosin B | 47.1 | 13.1 | 45.1 | 49.6 | 18.7 | 2.6 | 9.3 | 1.8 | * | * | * | * |
| free acid | x | x | x | x | 26.1 | 17.2 | 4.6 | 2.4 | * | * | * | * |
| phloxin B Na+ | * | * | * | * | x | x | x | x | x | x | 12.3 | 8.2 |
| | * | * | * | * | x | x | x | x | x | x | x | 8.7 |
| phloxin B | x | x | x | x | x | x | 35.6 | 23.7 | * | * | * | * |
| free acid | x | x | x | x | x | x | 230.6 | 82.8 | * | * | * | * |
| rose bengal Na+ | * | * | * | * | x | x | x | x | x | x | 8.9 | 7.9 |
| | * | * | * | * | x | x | x | x | x | x | 9.0 | 6.2 |
| rose bengal | x | x | x | 67.6 | 7.7 | 1.7 | 0.7 | + | * | * | * | * |
| free acid | x | x | x | x | x | x | x | x | * | * | * | * |
| Octabromofluorescein Na+ | * | * | * | * | x | x | x | x | x | x | x | x |
| | * | * | * | * | * | * | * | * | * | * | * | * |
| octabromofluorescein free acid | x | x | 41.9 | 41.6 | 25.6 | 21.4 | 9.4 | 5.8 | 1.5 | 0.9 | * | * |
| | * | * | * | * | * | * | * | * | * | * | * | * |
| fluorescein Na+ | * | * | * | * | x | x | x | x | x | x | x | x |
| | * | * | * | * | x | x | x | x | x | x | x | x |
| fluorescein | x | x | x | x | x | x | 23.5 | 19.6 | * | * | * | * |
| free acid | x | x | x | x | x | x | 44.1 | 17.9 | * | * | * | * |

+ Here and elsewhere in this specification, this indicates that there was an insignificant regression of the data to permit calculation of the $LC_{50}$ or $LT_{50}$ values because of total toxicity.

These results show that erythrosin B F.A. is approximately one order of magnitude more toxic than its sodium salt, the 24 hour $LC_{50}$ values being 21.0 and 22.6 ppm for the sodium salt and 1.1 and 3.3 ppm for the free acid. The sodium salt was not sufficiently toxic to permit calculation of the $LT_{50}$ values. However at the 12 ppm concentration level, the free acid generated $LT_{50}$ values of 1.8 and 2.4 hours in the two experiments.

The 24 hour $LC_{50}$ values for the sodium salt and the free acid form of phloxin B were similar, 17.1 and 13.4 ppm for the sodium salt and 14.2 and 24.8 ppm for the free acid. However, the 12 ppm $LT_{50}$ values indicate that the free acid has a more rapid kill time than the sodium salt at the concentration.

The tests with rose bengal sodium and its free acid show the free acid to be substantially more toxic than the salt, the 24 hour $LC_{50}$ values for the salt being 14.7 and 15.4 ppm and, in one experiment, 1.9 ppm for the free acid. The $LT_{50}$ values indicate a very rapid kill time and at quite low concentrations of the free acid (0.7 hour at 8 ppm) in comparison with the sodium salt. The results obtained in the second experiment gave insufficient regression to permit calculation of the $LC_{50}$ and $LT_{50}$ values.

Octabromofluorescein sodium salt is shown, both from the $LC_{50}$ and $LT_{50}$ data, to be essentially inactive as an insecticide. The free acid, on the other hand, showed a high degree of toxicity at concentrations as low as 2.6 ppm at 24 hours and a rapid kill time at 24 ppm ($LT_{50}$=1.5 hours).

The 24 hour $LC_{50}$ values for fluorescein free acid were 8.4 and 10.2 ppm, and the $LT_{50}$ values at 12 ppm were 19.6 and 17.9 hours. Under the same conditions, the salt showed no mortality after 24 hours of exposure and at concentrations as high as 192 ppm.

EXPERIMENT 2

In these parallel experiments, the effects of a dispersant, sodium lauryl sulfate (SLS), on the toxicities of the free acids of erythrosin B, phloxin B, rose bengal, octabromofluorescein and fluorescein were determined. For this purpose, samples of each of the free acids alone were prepared, as described in Experiment 1 above, and samples of the free acids containing 8% SLS were prepared by dispersing, with an Eppenbach Homo-Mixer, the free acids in water containing sufficient SLS to provide 8% of the latter based on P.C. of the acid and then spray drying the resulting dispersion. The results obtained in the toxicity test procedure against Culex larvae described above are set forth in Table IIa and Table IIb.

they were 12.1 and 10.8 ppm versus 5.0 and 5.6 ppm, an approximate twofold difference.

The same general picture emerges when viewing the $LT_{50}$ values at, for example, the 12 ppm concentration level, these values being, for erythrosin B, without and with SLS, 3.2 and 7.7 hours versus 0.4 and 0.3 hours; for phloxin B without and with SLS, 31.4 and 34.9 hours versus 0.3 and 0.4 hours; for rose bengal, without and with SLS, 1.6 hours in one experiment and a value too large to be determined in the other versus 0.4 and 0.8

TABLE IIa

| Compound | $LC_{50}$ (ppm)/Time (Hours) | | | | | | | | | | | |
|---|---|---|---|---|---|---|---|---|---|---|---|---|
| | 0.25 | 0.5 | 0.75 | 1.0 | 1.5 | 2 | 3 | 4 | 5 | 6 | 7 | 24 |
| erythrosin B F.A. (no SLS) | x | x | x | x | x | x | x | x | 7.4 | 7.4 | 17.4 | 5.4 |
| | x | x | x | x | x | 18.4 | 15.4 | 15.5 | 14.2 | 13.3 | 12.4 | 5.5 |
| erythrosin B F.A. (with 8% SLS) | x | 8.5 | 7.3 | 2.3 | 1.7 | 1.4 | 1.2 | 1.1 | 1.0 | 0.9 | 0.9 | 0.5 |
| | x | 6.3 | 3.3 | 2.1 | 1.6 | 1.3 | 1.1 | 0.9 | 0.9 | 0.8 | 0.8 | 0.5 |
| phloxin B F.A. (no SLS) | x | x | x | x | x | x | x | x | x | x | x | 13.5 |
| | x | x | x | x | x | x | x | x | x | x | x | 22.9 |
| phloxin B F.A. (with 8% SLS) | 14.0 | 6.5 | 4.3 | 3.0 | 2.4 | 1.6 | 1.3 | 1.0 | 0.9 | 0.8 | 0.7 | 0.5 |
| | x | 8.2 | 4.0 | 2.7 | 1.9 | 1.6 | 1.3 | 1.0 | 0.9 | 0.8 | 0.7 | 0.5 |
| rose bengal F.A. (no SLS) | x | x | x | 23.1 | 9.2 | 4.7 | 2.4 | 1.4 | 1.3 | 1.2 | 0.9 | 0.6 |
| | x | x | x | x | x | x | x | x | x | x | 75.2 | 33.0 |
| rose bengal F.A. (with 8% SLS) | x | 7.9 | 3.0 | 2.1 | 1.3 | 1.0 | 0.8 | 0.7 | 0.7 | 0.6 | 0.6 | 0.4 |
| | x | x | 16.2 | 9.1 | 6.2 | 3.9 | 2.8 | 2.3 | 2.3 | 2.0 | 1.9 | 1.1 |
| octabromofluorescein (no SLS) | * | x | x | 34.1 | 27.0 | 22.9 | 16.8 | 13.5 | 10.0 | 9.0 | 6.7 | 2.6 |
| | * | * | * | * | * | * | * | * | * | * | * | * |
| octabromofluorescein (with 8% SLS) | x | 11.3 | 7.2 | 4.2 | 2.8 | 2.0 | 1.4 | 1.0 | 0.8 | 0.6 | 0.5 | 0.2 |
| | * | * | * | * | * | * | * | * | * | * | * | * |
| fluorescein F.A. (no SLS) | x | x | x | x | x | x | 79.1 | 44.1 | 31.9 | 28.1 | 26.0 | 12.1 |
| | x | x | x | x | x | 42.8 | 34.6 | 30.2 | 25.9 | 24.6 | 22.9 | 10.8 |
| fluorescein F.A. (with 8% SLS) | x | x | x | x | x | x | 21.0 | 15.7 | 13.3 | 12.4 | 10.3 | 5.0 |
| | x | x | x | x | x | x | 11.7 | 10.5 | 9.9 | 9.1 | 8.6 | 5.6 |

TABLE IIb

| Compound | $LT_{50}$ (Hours)/Concns. (ppm) | | | | | | | | | |
|---|---|---|---|---|---|---|---|---|---|---|
| | .25 | .5 | .75 | 1 | 2 | 4 | 8 | 12 | 24 | 48 |
| erythrosin B F.A. (no SLS) | x | x | x | x | x | x | 3.6 | 3.2 | * | * |
| | x | x | x | x | 118.1 | 54.0 | 9.3 | 7.7 | * | * |
| erythrosin B F.A. (with 8% SLS) | x | 40.0 | 18.7 | 4.8 | 1.1 | 0.7 | 0.5 | 0.4 | * | * |
| | x | 26.0 | 7.3 | 3.9 | 1.1 | 0.6 | 0.5 | 0.3 | * | * |
| phloxin B F.A. (no SLS) | x | x | x | x | x | x | x | 31.4 | * | * |
| | x | x | x | x | x | x | x | 34.9 | * | * |
| phloxin B F.A. (with 8% SLS) | x | 26.2 | 8.6 | 4.6 | 2.1 | 0.9 | 0.4 | 0.3 | * | * |
| | 48.9 | 40.7 | 11.1 | 6.0 | 1.4 | 0.6 | 0.6 | 0.4 | * | * |
| rose bengal F.A. (no SLS) | * | * | 29.7 | 4.6 | 3.0 | 2.0 | 1.7 | 1.6 | 1.3 | 0.9 |
| | * | * | x | x | x | x | x | x | 34.7 | 14.8 |
| rose bengal F.A. (with 8% SLS) | 32.2 | 16.7 | 3.7 | 3.6 | 0.9 | 0.6 | 0.5 | 0.4 | * | * |
| | x | 36.0 | 14.8 | 14.5 | 10.3 | 8.3 | 1.1 | 0.8 | * | * |
| octabromofluorescein (no SLS) | x | x | 41.9 | 41.6 | 25.6 | 21.4 | 9.4 | 5.8 | 1.5 | 0.9 |
| | * | * | * | * | * | * | * | * | * | * |
| octabromofluorescein (with 8% SLS) | 16.0 | 6.5 | 5.6 | 4.4 | 3.3 | 1.6 | 0.8 | 0.5 | * | * |
| | * | * | * | * | * | * | * | * | * | * |
| fluorescein F.A. (no SLS) | x | x | x | x | x | x | 38.6 | 17.0 | 10.3 | 4.0 |
| | * | * | x | x | x | x | x | 15.0 | 6.4 | 2.2 |
| fluorescein F.A. (with 8% SLS) | x | x | x | x | x | 30.3 | 14.6 | 5.5 | * | * |
| | x | x | x | x | x | x | 9.2 | 3.4 | * | * |

These results show that, in all cases, the dispersant produced an increase in toxicity of the free acids, the difference being most evident in the SLS-containing erythrosin B, phloxin B, octabromofluorescein and rose bengal compositions. Thus the 24 hour $LC_{50}$ values for erythrosin B, without and with SLS, were 5.4 and 5.5 ppm versus 0.5 and 0.5 ppm, a tenfold difference; for phloxin B, without and with SLS, they were 13.5 and 22.9 ppm versus 0.5 and 0.5 ppm, an approximate thirty- to fortyfold difference; for rose bengal, without and with SLS, they were 0.6 and 33.0 ppm versus 0.4 and 1.1 ppm; for octabromofluorescein, without and with SLS, the single values obtained in each set of experiments were 0.6 ppm versus 0.2 ppm, an approximate tenfold difference; and for fluorescein, without and with SLS, hours; for octabromofluorescein without and with SLS, 5.8 hours versus 0.5 hours in the single set of experiments carried out with each composition; and for fluorescein, without and with SLS, 17.0 and 15.0 hours versus 5.5 and 3.4 hours.

EXPERIMENT 3

In order to verify the concept of the use of surfactants generally to increase the toxicity of the insecticidal free acid dyes, a series of compositions containing either erythrosin B F.A. or fluorescein F.A. and a variety of surfactants were prepared in the same manner as described in Experiment 2 above. The surfactants used in this study were:

EMULPHOR EL-719: General Aniline and Film brand of PEG 40 castor oil, a PEG derivative of castor oil with an average of 40 moles of ethylene oxide;

IGEPAL CO-630: General Aniline and Film brand of nonoxynol 10, an ethoxylated alkyl phenol of the formula $C_9H_{19}C_6H_4(OCH_2CH_2)_n$-OH where n has an average value of 10;

IGEPAL CO-880: General Aniline and Film brand of nonoxynol 30, an ethoxylated alkyl phenol of the formula $C_9H_{19}C_6H_4(OCH_2CH_2)_n$-OH where n has an average value of 30;

NEKAL BX-78: General Aniline and Film brand of sodium alkyl naphthalene sulfonate;

AQUONIUM C-IV: Hilton-Davis Chemical Co. brand of water soluble triazine-nucleated polymeric quaternary ammonium compounds described in U.S. Pat. No. 4,347,352;

SOLIDOGEN: General Aniline and Film brand of a liquid cationic resin; and

TAMOL N: Rohm and Haas brand of the sodium salt of condensed naphthalene sulfonic acid.

The results obtained in the toxicity test procedure against Culex larvae described above are set forth in Table IIIa and Table IIIb below:

TABLE IIIa

| Composition | $LC_{50}$ (ppm)/Time (Hours) | | | | | | | | | | | |
|---|---|---|---|---|---|---|---|---|---|---|---|---|
| | 0.25 | 0.5 | 0.75 | 1.0 | 1.5 | 2 | 3 | 4 | 5 | 6 | 7 | 24 |
| erythrosin B F.A. | x | x | 8.0 | 5.0 | 1.5 | 2.2 | + | + | + | + | + | + |
| 10% IGEPAL CO-630 | x | 14.2 | 5.3 | 2.2 | + | + | + | + | + | + | + | + |
| erythrosin B F.A. | x | x | 7.6 | 3.8 | 2.1 | 1.7 | + | + | + | + | + | + |
| 10% IGEPAL CO-880 | x | + | + | + | + | + | + | + | + | + | + | + |
| erythrosin B F.A. | x | 48.5 | 9.2 | 5.0 | 4.0 | 3.8 | 3.0 | 2.6 | 2.4 | 2.2 | + | + |
| 5% SLS | x | 5.8 | 4.0 | 3.2 | 2.5 | 2.3 | 2.1 | + | + | + | + | + |
| erythrosin B F.A. | x | 22.2 | 8.9 | + | + | + | + | + | + | + | + | + |
| 10% AQUONIUM C-IV | x | <2.0 | + | + | + | + | + | + | + | + | + | + |
| erythrosin B F.A. | 25.0 | + | + | + | + | + | + | + | + | + | + | + |
| 10% SOLIDOGEN LT-13 | x | <4.0 | + | + | + | + | + | + | + | + | + | + |
| erythrosin B F.A. | x | x | 34.8 | 14.8 | 13.4 | 9.9 | 7.5 | 6.8 | 5.8 | 5.4 | + | + |
| 5% TAMOL | x | 15.5 | 10.7 | 9.6 | <4.0 | <4.0 | + | + | + | + | + | + |
| fluorescein F.A. | x | x | x | x | x | x | x | 26.5 | 18.7 | 14.3 | 11.0 | 5.0 |
| 10% NEKAL BK-78 | x | x | x | x | x | x | x | 15.1 | 13.8 | 12.3 | 10.7 | 5.2 |
| fluorescein F.A. | x | x | x | x | x | x | x | x | x | x | 17.2 | 6.9 |
| 10% AQUONIUM C-IV | x | x | x | x | x | x | x | x | x | x | x | 7.5 |
| fluorescein F.A. | x | x | x | x | x | x | x | x | x | 16.5 | 11.1 | 3.3 |
| 10% EMULPHOR EL-719 | x | x | x | x | x | x | x | x | x | x | 18.3 | 5.8 |
| fluorescein F.A. | x | x | x | x | x | x | x | x | x | 17.5 | 15.0 | 7.5 |
| 8% SLS | x | x | x | x | x | x | x | x | x | 13.4 | 10.6 | 6.3 |

TABLE IIIb

| Composition | $LT_{50}$ (Hours)/Concns. (ppm) | | | | | | |
|---|---|---|---|---|---|---|---|
| | 1 | 2 | 4 | 8 | 10 | 12 | 24 |
| erythrosin B F.A. | * | * | 1.1 | 0.8 | 0.7 | 0.7 | 0.6 |
| 10% IGEPAL CO-630 | * | * | 0.9 | 0.7 | 0.6 | 0.6 | 0.3 |
| erythrosin B F.A. | * | * | 0.9 | 0.8 | 0.7 | 0.7 | 0.6 |
| 10% IGEPAL CO-880 | * | * | 1.0 | 0.5 | 0.6 | 0.6 | 0.3 |
| erythrosin B F.A. | * | 8.8 | 1.5 | 0.8 | * | 0.7 | 0.6 |
| 5% SLS | * | 3.9 | 0.7 | 0.6 | 0.4 | 0.2 | * |
| erythrosin B F.A. | * | 1.0 | 0.9 | 0.8 | 0.6 | 0.6 | * |
| 10% AQUONIUM C-IV | * | 0.5 | 0.5 | 0.4 | 0.5 | 0.6 | * |
| erythrosin B F.A. | * | * | 0.5 | 0.4 | + | + | + |
| 10% SOLIDOGEN LT-13 | * | * | 0.4 | 0.3 | 0.3 | 0.3 | 0.4 |
| erythrosin B F.A. | * | * | 16.1 | 4.6 | 2.3 | 1.8 | 0.8 |
| 5% TAMOL | * | * | 1.1 | 1.1 | 0.9 | 0.8 | 0.4 |
| fluorescein F.A. | x | x | 28.7 | 11.8 | * | 7.6 | * |
| 10% NEKAL BK-78 | x | x | 32.6 | 14.4 | * | 6.7 | * |
| fluorescein F.A. | x | x | x | 17.3 | * | 10.6 | * |
| 10% AQUONIUM C-IV | x | x | x | 17.8 | * | 12.9 | * |
| fluorescein F.A. | x | 23.5 | 20.2 | 9.9 | * | 10.2 | * |
| 10% EMULPHOR EL-719 | x | 26.5 | 16.8 | * | 12.2 | * | |
| fluorescein F.A. | x | x | x | 17.0 | * | 12.1 | * |

TABLE IIIb-continued

| Composition | $LT_{50}$ (Hours)/Concns. (ppm) | | | | | | |
|---|---|---|---|---|---|---|---|
| | 1 | 2 | 4 | 8 | 10 | 12 | 24 |
| 8% SLS | x | x | x | 11.3 | * | 8.6 | * |

These results show that there are no substantial differences in the toxicities of erythrosin B F.A. and fluorescein F.A. due to the different dispersants. Thus the 1 hour $LC_{50}$ values for the erythrosin B F.A. containing formulations with 10% IGEPAL CO-630, 5% SLS and the single value obtained for IGEPAL CO-880 were essentially the same. TAMOL N appeared to be effective, but less so than IGEPAL CO-630, IGEPAL CO-880 and SLS. The values for the erythrosin B free acid formulations with SOLIDOGEN and AQUONIUM C-IV were quite low but could not be quantified. The $LT_{50}$ values at the 24 ppm concentration for the erythrosin B free acid formulations were all below 1 hour.

In the fluorescein-containing formulations, the $LC_{50}$ values at the 24 hour period were all quite similar as were the $LT_{50}$ values at the 12 ppm concentration level.

EXPERIMENT 4

In order to determine whether the results obtained in Experiment 3 above could be attributed in any degree to inherent toxicity of the various dispersants used therein, the concentrations of each of the dyes in the dye/dispersant compositions used in Experiment 3 above were calculated, and that amount of dispersant alone was tested for its toxicity against Culex larvae at a standard concentration of 8.0 ppm at the same time intervals used throughout Experiments 1-3 above. The amounts of each of the dispersants so-calculated based on the P.C. of the dyes and the concentrations at which they were tested were as follows:

TABLE IV

| Dispersant | % Based on % P.C. of Dyes | Concn. (ppm) |
|---|---|---|
| 10% AQUONIUM C-IV | 84.3% | 8.0 |
| 10% AQUONIUM C-IV | 8.9% | 8.0 |
| 10% EMULPHOR EL-719 | 92.0% | 8.0 |
| 10% IGEPAL CO-630 | 11.5% | 8.0 |
| 10% IGEPAL CO-880 | 12.6% | 8.0 |
| 10% SOLIDOGEN | 11.6% | 8.0 |
| 5% TAMOL N | 12.9% | 8.0 |
| 10% NEKAL BK-78 | 80.0% | 8.0 |

TABLE IV-continued

| Dispersant | % Based on % P.C. of Dyes | Concn. (ppm) |
|---|---|---|
| 8% SLS | 91.9% | 8.0 |
| 8% SLS | 4.5% | 4.0 |

None of these compositions produced mortality in any of the test compositions at any time interval. Thus the insecticidal activities of the dye/dispersant compositions observed in Experiment 3 cannot be attributable to the dispersants.

EXPERIMENT 5

In this experiment, the effect of mixing fluorescein free acid with each of erythrosin B free acid and rose bengal free acid at 1:1 and 3:1 ratios of fluorescein F.A. to the other two free acids without any dispersants was studied. For this purpose the necessary amounts of the sodium salts of fluorescein and erythrosin and fluorescein and rose bengal to give molar ratios of 1:1 and 3:1 based on P.C.'s of the dye samples were dissolved in water and the solution acidified to pH 0.4 by addition of hydrochloric acid to thus co-precipitate the two free acids. The solids so-obtained were then subjected to dispersion with an Eppenbach Homo-Mixer, and the resulting dispersions were then spray dried. The test samples thus prepared were tested against Culex larvae using the toxicity test procedure described above. The results so obtained are set forth in Table Va and Table Vb below:

ity than the corresponding 3:1 formulations. However the data do not indicate that the toxicities of the mixtures are significantly greater than the toxicities of the individual components.

EXPERIMENT 6

In order to determine whether added dispersants would increase the toxicity of 1:1 or 3:1 combinations of fluorescein F.A. with erythrosin B or rose bengal F.A.'s, the procedure of Experiment 5 above was repeated using the co-precipitated free acids containing, in each case, 8% SLS based on total P.C. of the dyes. For this study, two 1:1 formulations of fluorescein F.A.-:erythrosin B F.A. (Formulations A and B), a 1:1 combination of fluorescein F.A.:rose Bengal F.A. and a 3:1 combination of fluorescein F.A.:rose bengal F.A. were prepared. The 1:1 fluorescein F.A.:erythrosin B F.A. formulation (Formulation A) and the 1:1 and 3:1 fluorescein F.A.:rose bengal F.A. formulations were prepared by suspending the free acids in appropriate molar ratios with respect to one another in water and adjusting the pH to 9.5 by the addition of solid sodium hydroxide until the solids dissolved. The resulting solutions were then added slowly with stirring to aqueous hydrochloric acid, and the solids which separated, consisting of the co-precipitated free acids, were collected in each case, and then suspended in water. Sufficient SLS was added to provide 8% SLS based on total moles of free acids, the solutions were stirred with an Eppenbach Homo-Mixer until all solids had become dispersed, and the dispersions were then spray dried.

TABLE Va

| | LC$_{50}$ (ppm)/Time (Hours) | | | | | | | | | | | |
|---|---|---|---|---|---|---|---|---|---|---|---|---|
| | 0.25 | 0.5 | 0.75 | 1.0 | 1.5 | 2 | 3 | 4 | 5 | 6 | 7 | 24 |
| fluorescein/ery- | x | x | x | x | x | x | x | 15.5 | 23.6 | 21.8 | 10.2 | 5.3 |
| throsin F.A.'s 1:1 | x | x | x | x | x | x | x | 27.1 | 21.6 | 20.3 | 19.9 | 14.0 |
| fluorescein/ery- | x | x | x | x | x | x | x | x | x | x | ·x | 12.1 |
| throsin F.A.'s 3:1 | x | x | x | x | x | x | x | x | x | x | x | 40.0 |
| fluorescein/rose | x | x | 9.5 | + | + | + | + | + | 2.4 | + | + | + |
| bengal F.A.'s 1:1 | x | x | x | x | x | x | x | x | x | x | x | 8.6 |
| fluorescein/rose | x | + | + | + | + | + | + | + | + | + | + | + |
| bengal F.A.'s 3:1 | x | x | x | x | x | x | x | x | x | x | x | 27.8 |
| fluorescein F.A. | x | x | x | x | x | x | 10.9 | 7.3 | 5.4 | 4.5 | 4.3 | 1.5 |
| | x | x | x | 52.9 | 22.0 | 18.8 | 16.9 | 16.2 | 15.4 | 15.5 | 14.7 | 10.9 |
| rose bengal | x | x | 6.0 | 4.1 | 2.8 | 2.3 | 2.0 | 1.5 | 1.1 | 1.1 | + | + |
| F.A. | x | x | x | x | x | x | x | x | x | x | x | 10.0 |
| erythrosin B | x | x | x | x | x | x | x | x | x | x | x | 1.1 |
| F.A. | x | x | 39.4 | 19.1 | 19.9 | 14.2 | 7.9 | 6.8 | 6.4 | 6.0 | 5.7 | 3.3 |

TABLE Vb

| | LT$_{50}$ (Hours)/Concn. (ppm) | | | | | | | | | | | | |
|---|---|---|---|---|---|---|---|---|---|---|---|---|---|
| | 0.5 | 1 | 2 | 3 | 4 | 6 | 8 | 9 | 12 | 18 | 24 | 36 | 48 |
| fluorescein/ery- | x | x | x | * | x | * | 8.7 | * | 6.4 | * | 2.8 | * | * |
| throsin F.A.'s 1:1 | x | x | x | * | x | * | x | * | 41.2 | * | 5.0 | * | * |
| fluorescein/ery- | * | x | x | * | 37.5 | * | 37.0 | * | 15.8 | * | 13.0 | * | * |
| throsin F.A.'s 3:1 | x | x | x | * | x | * | x | * | 40.0 | * | 41.4 | * | * |
| fluorescein/rose | * | * | 5.0 | * | 4.1 | 3.6 | * | * | 0.4 | * | 0.1 | * | * |
| bengal F.A.'s 1:1 | * | * | x | * | x | 91.4 | * | * | 36.7 | * | 5.5 | * | * |
| fluorescein/rose | * | * | * | * | 1.7 | * | 1.5 | * | 1.2 | * | 1.2 | * | 0.4 |
| bengal F.A.'s 3:1 | * | * | * | * | x | * | x | * | x | * | 26.7 | * | 15.9 |
| fluorescein | * | x | 19.5 | 9.6 | * | 4.3 | * | 2.9 | 2.5 | 2.1 | * | 1.9 | * |
| F.A. | * | x | x | x | * | x | * | 40.3 | 35.0 | 2.6 | * | 1.2 | * |
| rose bengal | * | 5.4 | 3.6 | 2.5 | * | 0.9 | * | * | 0.3 | * | * | * | * |
| F.A. | * | x | x | x | * | 109.9 | * | * | 20.1 | * | * | * | * |
| erythrosin B | 13.1 | 49.6 | 18.7 | * | 2.6 | * | 9.3 | * | 1.8 | * | * | * | * |
| F.A. | x | x | 26.1 | * | 17.2 | * | 4.6 | * | 2.4 | * | * | * | * |

These results, whether viewed from the 24 hours LC$_{50}$ or the 12 ppm LT$_{50}$ values, show that the 1:1 fluorescein:erythrosin F.A. and the 1:1 fluorescein:rose bengal F.A. formulations have generally greater toxic- A second formulation of 1:1 fluorescein F.A.:erythrosin B F.A. containing 8% SLS (Formulation B) was prepared by a modified procedure in which equimolar amounts of fluorescein F.A. and erythrosin B F.A. were dissolved by addition of alkali and the resulting solution treated with dilute hydrochloric acid to effect separation of the free acids. The collected solids were then collected and suspended in water containing sufficient SLS to provide 8% SLS in the final mixture based on total free acids. The solids were dispersed first by stirring with a malt mixer and then by stirring with an Eppenbach Homo-Mixer for one hour and the dispersion then spray dried.

The results obtained against Culex larvae in the toxicity test procedure described above using each of these formulations are set forth in Table VIa and Table VIb below. Corresponding data for each of the individual free acids (fluorescein F.A., erythrosin B F.A. and rose bengal F.A.), each containing 8% SLS, are included for comparative purposes.

F.A. formulation (0.3 ppm in the single experiment for which a value could be calculated) with fluorescein F.A. with SLS (5.0 and 5.6 ppm) or with rose bengal F.A. with SLS (0.4 and 1.1 ppm).

Similar differences in toxicity are seen when comparing the 2 hour $LT_{50}$ values for the 1:1 fluorescein:erythrosin B free acids [0.5 hour and <0.5 hour (Formulation A) or 0.6 and 0.4 hour (Formulation B)] with fluorescein free acid with SLS (concentration too high to permit calculation of a result) or with erythrosin B F.A. with SLS (1.1 hour in both experiments); and when comparing the same values for 1:1 fluorescein:rose bengal F.A.'s (0.6 and 2.1 hours) with fluorescein F.A. alone (concentration too high to be calculated) or with rose bengal alone (0.9 and 10.3 hours).

EXPERIMENT 7

TABLE VIa

| | $LC_{50}$ (ppm)/Time (Hours) | | | | | | | | | | | |
|---|---|---|---|---|---|---|---|---|---|---|---|---|
| | 0.25 | 0.50 | 0.75 | 1.0 | 1.5 | 2 | 3 | 4 | 5 | 6 | 7 | 24 |
| fluorescein/ery- | x | 1.5 | 0.9 | 0.7 | 0.6 | 0.5 | 0.5 | 0.5 | 0.4 | 0.3 | 0.3 | + |
| throsin F.A.'s 1:1 | x | 2.0 | 0.9 | 0.7 | 0.5 | 0.5 | 0.4 | 0.4 | 0.4 | 0.3 | 0.3 | 0.2 |
| (Formulation A) | | | | | | | | | | | | |
| fluorescein/ery- | x | x | 1.2 | 1.0 | 0.8 | 0.6 | 0.4 | 0.4 | 0.3 | 0.3 | 0.3 | + |
| throsin F.A.'s 1:1 | x | x | 0.8 | 0.7 | 0.6 | 0.6 | 0.6 | 0.5 | 0.5 | 0.5 | 0.5 | 0.2 |
| (Formulation B) | | | | | | | | | | | | |
| fluorescein/rose | 6.9 | 2.8 | 1.8 | 1.3 | + | + | + | + | + | + | + | + |
| bengal F.A.'s 1:1 | x | x | x | x | x | x | <1.0 | <1.0 | <1.0 | 0.3 | 0.2 | 0.3 |
| fluorescein/rose | 6.5 | 3.0 | 2.4 | + | + | + | + | + | + | + | + | + |
| bengal F.A.'s 3:1 | x | 10.9 | 5.1 | 3.2 | 1.8 | 1.3 | 1.0 | 1.0 | 1.0 | 0.9 | 0.9 | + |
| fluorescein F.A. | x | x | x | x | x | x | 21.0 | 15.7 | 13.3 | 12.4 | 10.3 | 5.0 |
| with SLS | x | x | x | x | x | x | 11.7 | 10.7 | 9.9 | 9.1 | 8.6 | 5.6 |
| erythrosin B F.A. | x | 8.5 | 7.3 | 2.3 | 1.7 | 1.4 | 1.2 | 1.1 | 1.0 | 0.9 | 0.9 | 0.5 |
| with SLS | x | 6.3 | 3.3 | 2.1 | 1.6 | 1.3 | 1.1 | 0.9 | 0.9 | 0.8 | 0.8 | 0.5 |
| rose bengal | x | 7.9 | 3.0 | 2.1 | 1.3 | 1.0 | 0.8 | 0.7 | 0.7 | 0.6 | 0.6 | 0.4 |
| F.A. with SLS | x | x | 16.2 | 9.1 | 6.2 | 3.9 | 2.8 | 2.3 | 2.3 | 2.0 | 1.9 | 1.1 |

TABLE VIb

| | $LT_{50}$ (Hours)/Concn. (ppm) | | | | | | | | | | | | | |
|---|---|---|---|---|---|---|---|---|---|---|---|---|---|---|
| | .25 | .50 | .75 | 1.0 | 1.5 | 2 | 3 | 4 | 6 | 8 | 9 | 12 | 18 | 24 |
| fluorescein/ery- | 9.6 | 4.1 | 1.0 | 0.8 | * | 0.5 | * | * | * | * | * | * | * | * |
| throsin F.A.'s 1:1 | 13.1 | 1.8 | 1.3 | 0.7 | * | <0.5 | * | * | * | * | * | * | * | * |
| (Formulation A) | | | | | | | | | | | | | | |
| fluorescein/ery- | 5.8 | 4.3 | 1.5 | 1.0 | * | 0.6 | * | * | * | * | * | * | * | * |
| throsin F.A.'s 1:1 | 23.6 | 10.1 | 0.7 | 0.7 | * | 0.4 | * | * | * | * | * | * | * | * |
| (Formulation B) | | | | | | | | | | | | | | |
| fluorescein/rose | * | * | * | 1.5 | * | 0.6 | * | 0.4 | + | * | * | + | * | * |
| bengal F.A.'s 1:1 | * | * | * | 3.4 | * | 2.1 | * | 2.1 | 1.2 | 1.2 | * | + | * | * |
| fluorescein/rose | * | * | * | * | * | 1.3 | * | 0.2 | * | 0.2 | * | + | * | * |
| bengal F.A.'s 3:1 | * | * | * | * | * | 1.6 | * | 1.0 | * | 0.7 | * | 0.5 | * | 0.3 |
| fluorescein F.A. | x | x | x | x | * | x | * | 30.3 | * | 14.6 | * | 5.5 | * | * |
| with SLS | x | x | x | x | * | x | * | x | * | 9.2 | * | 3.4 | * | * |
| erythrosin F.A. | x | 40.0 | 18.7 | 4.8 | * | 1.1 | * | 0.7 | * | 0.5 | * | 0.4 | * | * |
| with SLS | x | 26.0 | 7.3 | 3.0 | * | 1.1 | * | 0.6 | * | 0.5 | * | 0.3 | * | * |
| rose bengal | 32.2 | 16.7 | 3.7 | 3.6 | * | 0.9 | * | 0.6 | * | 0.5 | * | 0.4 | * | * |
| F.A. with SLS | x | 36.0 | 14.8 | 14.5 | * | 10.3 | * | 8.6 | * | 1.1 | * | 0.8 | * | * |

These results again show that there is no significant difference between the toxicities of fluorescein F.A. and rose bengal F.A. at 1:1 and 3:1 ratios. However the data also show that when 1:1 mixtures of fluorescein and erythrosin B free acids or fluorescein and rose bengal free acids are formulated with 8% SLS, the toxicities are substantially increased over the toxicities of either of the separate free acids in combination with SLS. This is evident when comparing the 24 hour $LC_{50}$ values for the fluorescein:erythrosin free acids (0.2 ppm in each of the experiments involving Formulations A and B for which values could be calculated) with fluorescein F.A. with added SLS (5.0 and 5.6 ppm) or erythrosin B F.A. with added SLS (0.5 and 0.5 ppm) or when comparing the same values for the 1:1 fluorescein F.A.:rose bengal In order to determine whether other forms of the xanthene dyes, such as the aluminum lakes thereof, would be effective against Culex larvae, the toxicity of erythrosin B F.A. with 8% SLS, as used in Experiment 2, was compared with the toxicity of erythrosin B aluminum lake, with and without added SLS. For this purpose, erythrosin B aluminum lake without SLS was purchased commercially and used as such.

The corresponding erythrosin B aluminum lake with 8% SLS was prepared by adding an aqueous solution containing sufficient SLS to provide 8% SLS in the final mixture to erythrosin B aluminum lake and stirring to produce a paste. Additional water was added to the paste to provide a thin dispersion which was then subjected to fine dispersion by stirring with an Eppenbach Homo-Mixer and then spray drying.

The results obtained against Culex larvae in the toxicity test procedure described above using these formulations are set forth in Table VIIa and Table VIIb.

TABLE VIIa

|  | $LC_{50}$ (ppm)/Time (Hours) |  |  |  |  |  |  |  |  |  |  |
|---|---|---|---|---|---|---|---|---|---|---|---|
|  | 0.25 | 0.5 | 0.75 | 1.0 | 1.5 | 2 | 3 | 4 | 5 | 6 | 7 | 24 |
| erythrosin B F.A. | x | 7.2 | 3.7 | 2.3 | 1.9 | + | + | + | + | + | + | 1.0 |
| (with SLS) | x | 5.2 | 2.2 | 2.5 | 2.3 | 2.2 | 1.8 | 1.7 | 1.6 | 1.5 | 1.4 | 0.8 |
| erythrosin B Al | x | x | 11.9 | 5.3 | 3.5 | 2.6 | 2.4 | 2.2 | 2.0 | 1.8 | 1.7 | + |
| lake (wth SLS) | x | x | 4.9 | 2.4 | 1.9 | 1.5 | 1.2 | 1.1 | 1.0 | 0.9 | 0.9 | 0.7 |
| erythrosin B Al | x | x | x | x | x | x | x | x | x | x | x | 10.1 |
| lake (without SLS) | x | x | x | x | x | x | x | x | x | x | x | 9.5 |

TABLE VIIb

|  | $LT_{50}$ (Hours)/Concn. (ppm) |  |  |  |  |
|---|---|---|---|---|---|
|  | 0.5 | 1.0 | 2 | 4 | 8 |
| erythrosin B F.A. | x | 25.2 | 1.3 | 0.7 | 0.5 |
| (with SLS) | x | 16.7 | 3.7 | 0.5 | 0.4 |
| erythrosin B Al | x | 10.6 | 8.0 | 1.6 | 0.9 |
| lake (with SLS) | x | 6.9 | 1.6 | 0.9 | 0.7 |
| erythrosin B Al | x | x | x | x | 42.7 |
| lake (without SLS) | x | x | x | 61.0 | 32.7 |

These results show that the toxicities of erythrosin B F.A. with SLS and erythrosin B aluminum lake with SLS are quite similar, whereas the aluminum lake without SLS is substantially less toxic as indicated by the 24 hour $LC_{50}$ values (1.0 and 0.8 ppm for the free acid with SLS; 0.7 ppm for the aluminum lake with SLS in the one experiment where a result could be calculated; and 10.1 and 9.5 ppm for the lake without SLS).

Similar conclusions can be drawn from a consideration of the $LT_{50}$ values at the 8 ppm concentration level (0.5 and 0.4 hours for the free acid with SLS; 0.9 and 0.7 hours for the aluminum lake with SLS; and 42.7 and 32.7 hours for the aluminum lake without SLS).

EXPERIMENT 8

In order to test the efficacy of mixtures of aluminum lakes, the toxicity of a 1:1 mixture of co-precipitated fluorescein free acid:erythrosin B free acid with 8% SLS, prepared as described in Example 6 above, was compared with the toxicities of physical and chemical blends of 1:1 mixtures of the aluminum lakes of fluorescein and erythrosin, each also containing 8% SLS.

The physical blend of the aluminum lakes was prepared by stirring equimolar amounts of the aluminum lakes of fluorescein and erythrosin B in tap water until all solids were suspended, adding an aqueous solution containing sufficient SLS to provide 8% SLS in the final mixture, stirring the mixture again for five minutes, subjecting the mixture to dispersion with an Eppenbach Homo-Mixer and spray drying the resulting dispersion.

The erythrosin B aluminum lake used for the preparation of the physical blend described above was obtained commercially.

The fluorescein lake used was prepared as follows: an aqueous solution of aluminum chloride was added, with stirring, to a solution of sodium carbonate in water, the alumina hydrate which separated was allowed to settle, and excess water was decanted from the mixture. The mixture was then treated with sodium acetate with stirring and then with a solution containing fluorescein sodium in water followed by an additional amount of aluminum chloride, corresponding approximately to 33% of the original quantity added. After heating the mixture to 65° C., the lake which separated was collected by filtration.

The chemical blend of the aluminum lakes was prepared as follows: an aqueous solution of aluminum chloride was added with stirring to a solution of sodium carbonate in water, the alumina hydrate which formed was allowed to settle, and excess water was decanted from the mixture. The mixture was then treated with stirring with sodium acetate followed by a solution containing equimolar amounts of erythrosin B sodium and fluorescein sodium in water. the mixture was then treated with an additional quantity of aluminum chloride solution, corresponding approximately to about 33% of the original amount added. The mixture was heated to 65° C. and the lake collected by filtration. The product was stirred in tap water for fifteen minutes, the suspension subjected to dispersion with an Eppenbach Homo-Mixer, additional tap water containing sufficient SLS to provide 8% SLS in the final product was added, the mixture was again subjected to dispersion with an Eppenbach Homo-Mixer, and the dispersion was then spray dried.

the toxicities of the compositions were then determined against Culex larvae using the toxicity test procedure described above. The results obtained are set forth in Table VIIIa and Table VIIIb below.

TABLE VIIIa

|  | $LC_{50}$ (ppm)/Time (Hours) |  |  |  |  |  |  |  |  |  |  |
|---|---|---|---|---|---|---|---|---|---|---|---|
|  | 0.25 | 0.5 | 0.75 | 1 | 1.5 | 2 | 3 | 4 | 5 | 6 | 7 | 24 |
| Co-precipitated | x | x | x | x | x | x | x | 1.7 | 1.5 | 1.3 | 1.2 | 0.6 |
| 1:1 fluorescein/ | x | x | x | x | 2.1 | 1.6 | 1.3 | 1.2 | 1.0 | 1.0 | 0.9 | 0.5 |
| erythrosin B F.A.'s |  |  |  |  |  |  |  |  |  |  |  |  |
| Co-precipitated 1:1 | x | x | x | x | x | x | x | x | x | x | x | 1.6 |
| fluorescein/erythrosin B | x | x | x | x | x | x | x | x | x | x | x | x |
| Al lakes (Physical) |  |  |  |  |  |  |  |  |  |  |  |  |
| Chemical blend Al | x | x | x | x | x | x | x | x | x | x | x | 2.3 |
| lakes of fluorescein/ | x | x | x | x | x | x | x | x | x | x | x | x |
| erythrosin B |  |  |  |  |  |  |  |  |  |  |  |  |

TABLE VIIIb

|  | $LT_{50}$ (Hours)/Concn. (ppm) | | | | |
| --- | --- | --- | --- | --- | --- |
|  | 0.25 | 0.50 | 0.75 | 1.0 | 2.0 |
| Co-precipitated 1:1 fluorescein/erythrosin B F.A.'s | 47.6 | 41.4 | 18.5 | 8.4 | 3.1 |
|  | x | 39.1 | 7.5 | 7.7 | 1.6 |
| Co-precipitated 1:1 fluorescein/erythrosin B Al lakes (Physical) | x | x | x | 55.4 | 18.5 |
|  | x | x | x | x | x |
| Chemical blend Al lakes of fluorescein/erythrosin B | x | x | x | x | 30.1 |
|  | x | x | x | x | x |

These results show that, although both the physical and the chemical blends of the fluorescein:erythrosin aluminum lakes were effective as photodynamically toxic insecticides, the free acid mixture was more effective. Thus the 24 hour $LC_{50}$ values for 1:1 mixtures of fluorescein:erythrosin B free acids were 0.6 and 0.5 ppm in comparison with 1.6 ppm and 2.3 ppm, respectively, for the physical and the chemical blends of the aluminum lakes in the single experiments involving the lakes where $LC_{50}$ values could be calculated. Likewise the $LT_{50}$ values at the 2.0 ppm concentration level showed the 1:1 fluorescein:erythrosin B free acid mixture to produce much shorter kill times (3.1 and 1.6 hours) than the physical and the chemical blends of the lakes (18.5 and 30.1 hours, respectively, in the two experiments involving the lakes where $LT_{50}$ values could be calculated).

EXPERIMENT 9

In order to test a representative composition of the invention under field use conditions, a field test against mosquitoes was carried out as follows. A total of 21 holes, each measuring 1 meter wide, 1 meter long and ¼ meter deep, were dug into the soil, the holes were lined with plastic sheets, filled to a depth of approximately 25 cm. with water and then covered with screens to exclude other insects.

The test organisms used for the experiment were fourth instar larvae of *Culex pipiens quinquefasciatus* which were harvested from a laboratory colony, and groups of 100 larvae were placed in each of the test holes.

A spray dried form of erythrosin B free acid containing 8% SLS, similar to that used in Experiment 2 described above, was chosen as the test composition. Samples of the test dye were weighed out to provide the range of effective concentrations given in Table IXa below, the weight of the dye being adjusted according to the percent purity (i.e. the P.C.) of the dye. Weighed samples were then sealed in foil envelopes and stored in darkness until used.

TABLE IXa

| Sample Weight Applied (mg/m²) | Effective Concn. (ppm) |
| --- | --- |
| 6.330 | 0.25 |
| 12.661 | 0.50 |
| 25.321 | 1.00 |
| 50.643 | 2.00 |
| 101.286 | 4.00 |
| 202.572 | 8.00 |

At the commencement of each experiment, pretreatment larvae population samples were taken in each hole by making four dips around the perimeter of the holes with a sampling scoop (about 200 ml. each), and the larvae in each dip were counted and recorded.

For each test, 18 of the holes were treated with the weighed out dye samples, 3 holes at each of the six concentrations given in Table IXa above, and an additional 3 holes were left untreated to serve as controls. Thus each dye concentration and each control were replicated three times. The dye samples were added to the plots by dropping them onto the water surface with brief stirring to aid distribution.

In a first test, larval post-treatment population samples were taken in each hole 24 hours after dye application using the same sampling procedure used for the pretreatment samples. Results obtained in the 24 hour test are given in Table IXb below, each value being an average of larval counts of the four sampling dips made in each of the three-replicate tests carried out at each concentration. Thus each larval count shown in the table is an average of twelve individual counts.

TABLE IXb

|  | Larval Population[a] | |
| --- | --- | --- |
| Concn. (ppm) | Pre-treatment | Post-treatment |
| 0.00 | 2.9 A | 2.7 A |
| 0.25 | 2.8 A | 3.3 A |
| 0.50 | 2.1 A | 3.4 A |
| 1.00 | 1.3 A | 1.4 A |
| 2.00 | 2.1 A | 3.0 A |
| 4.00 | 2.9 A | 2.8 A |
| 8.00 | 2.3 A | 2.4 A |

[a]Column entries in this and the following tables at each concentration level which are not followed by the same letter are significantly different at the 0.05 level.

These results show that, under field use conditions, a twenty-four hour exposure period is insufficient, at all concentration levels tested, to effect any significant reduction in the larval population.

Accordingly, three tack-traps were then deployed in each hole to capture adult insects emerging from the test holes, the screen top was replaced, and thirteen days later each hole was sampled as before to obtain larval counts. Adults captured by the tack-traps were also counted. Results obtained, in two separate thirteen day experiments, are given in Tables IXc and IXd below. As in the previous procedure, each larval count represents an average of twelve individual counts (i.e. four sampling dips in each of the three replicate tests at each concentration). Each adult count represents an average of nine individual counts (i.e. three tack-traps in each hole in each of the three replicate test).

TABLE IXc

|  | Larval Population | | Adult |
| --- | --- | --- | --- |
| Concn. (ppm) | Pre-treatment | Post-treatment | Emergence |
| 0.00 | 5.1 A | 6.0 A | 43.9 A |
| 0.25 | 6.1 A | 4.1 AB | 25.3 B |
| 0.50 | 5.0 A | 3.8 AB | 5.7 C |
| 1.00 | 4.3 A | 1.3 BC | 1.9 C |
| 2.00 | 4.3 A | 0.9 BC | 4.0 C |
| 4.00 | 3.4 A | 0.3 C | 2.0 C |

TABLE IXc-continued

| Concn. (ppm) | Larval Population | | Adult Emergence |
| --- | --- | --- | --- |
| | Pre-treatment | Post-treatment | |
| 8.00 | 5.0 A | 0.2 C | 1.7 C |

TABLE IXd

| Concn. (ppm) | Larval Population | | Adult Emergence |
| --- | --- | --- | --- |
| | Pre-treatment | Post-treatment | |
| 0.00 | 6.1 A | 7.3 A | 19.4 A |
| 0.25 | 6.3 A | 6.6 AB | 21.8 A |
| 0.50 | 5.2 A | 9.1 A | 17.2 A |
| 1.00 | 6.4 A | 1.0 C | 3.2 B |
| 2.00 | 6.4 A | 1.9 BC | 2.6 B |
| 4.00 | 4.7 A | 0.0 C | 3.9 B |
| 8.00 | 6.1 A | 0.5 C | 2.3 B |

These results demonstrate that erythrosin B free acid, containing sodium lauryl sulfate as a dispersant, is not only effective in combatting mosquitoes in a laboratory test environment, as shown for example in Experiment 2 above, it is also effective at varying use concentrations in combatting these insects in a natural field environment.

Although the test procedures described above were, for the sake of convenience, carried out on a single species of the family Culicidae, of the order Diptera, the compositions are shown by the results obtained to manifest their toxic effect by a photodynamically mediated pathway. It is thus contemplated that the compositions and the methods of the invention can be used to combat any adult insects or insect larvae which, in the course of their normal life cycle, become exposed to visible light. Such other insects would include not only other members of the family Culicidae, such as the sub-families Culinae and Corethrinae thereof, and other genera, besides Culex, of such sub-families, such as Anopheles and Stegomyia (Aedes), but also other families of the order Diptera, including members of the family Muscidae, such as *Musca domestica, Musca autumnalis, Musca luteola* and *Musca vomitoria*.

In combatting all such insects and their larvae, it is only necessary to treat the environment in which such insects live or breed with the compositions of the invention and then permit exposure of the treated environment either to sunlight or to artificial visible light.

We claim:

1. The method of combatting adult insects or insect larvae which comprises causing the insects or their larvae to ingest an insecticidally effective amount of an insecticidal composition selected from the group consisting of the water-insoluable free acids of (A) erythrosin B, rose bengal octabromofluorescein or fluorescein; (B) the aluminum lakes thereof; and (C) mixtures of (A) or (B), whereby the insects or insect larvae die upon thereafter being exposed to visible light.

2. The method according to claim 1 of combatting insects of the family Culicidae.

3. The method according to claim 2 wherein the insecticidally effective composition comprises one of the free acids of erythrosin B, rose bengal, octabromofluorescein or fluorescein or an aqueous dispersion thereof.

4. The method according to claim 2 wherein the insecticidally effective composition comprises (A) a mixture of two or more of the free acids of erythrosin B, rose bengal, octabromofluorescein or fluorescein; (B) a mixture of the aluminum lakes thereof; or an aqueous dispersion of (A) or (B).

5. The method of claim 3 wherein the insecticidal composition is combined with a dispersant.

6. The method of claim 4 wherein the insecticidal composition is combined with a dispersant.

7. The method of combatting adult insects or insect larvae which comprises treating an environment in which said insects live or breed with an insecticidal composition containing an insecticidally effective amount of a member of the group consisting of the Water-insoluble free acids of (A) erythrosin B, rose bengal, octabromofluorescein or fluorescein; (B) the aluminum lakes thereof; and (C) mixtures of (A) or (B).

8. The method according to claim 7 of combatting insects of the family Culicidae.

9. The method according to claim 8 wherein the insecticidally effective composition comprises one of the free acids of erythrosin B, rose bengal, octabromofluorescein or fluorescein or an aqueous dispersion thereof.

10. The method according to claim 8 wherein the insecticidally effective composition comprises (A) a mixture of two or more of the free acids of erythrosin B, rose bengal, octabromofluorescein or fluorescein; (B) a mixture of the aluminum lakes thereof; or an aqueous dispersion of (A) or (B).

11. The method of claim 9 wherein the insecticidal composition is combined with a dispersant.

12. The method of claim 10 wherein the insecticidal composition is combined with a dispersant.

13. A water insoluble, photodynamic insecticidal composition effective against adult insects or insect larvae which comprises an insecticidally effective amount of (A) a member of the group consisting of the free acids of erythrosin B, rose bengal, octabromofluorescein and fluorescein; (B) the aluminum lakes of said erythrosin B, rose bengal or octabromofluorescein; (C) mixtures of (A) or (B); or (D) an aqueous dispersion of (A), (B) or (C) in combination with a dispersant.

14. A composition according to claim 13 wherein the effective insecticidal composition comprises a member of the group consisting of one of the free acids of erythrosin B, rose bengal, octabromofluorescein and fluorescein or an aqueous dispersion of the same.

15. A composition according to claim 13 wherein the effective insecticidal composition comprises a member of the group consisting of (A) a mixture of two or more of the free acids of erythrosin B, rose bengal, octabromofluorescein or fluorescein; and (B) a mixture of the aluminum lakes thereof; or an aqueous dispersion of (A) or (B).

16. A composition according to claim 14 containing erythrosin B free acid in dry powder form or an aqueous dispersion thereof.

17. A composition according to claim 14 containing rose bengal free acid in dry powder form on an aqueous dispersion thereof.

18. A composition according to claim 14 containing octabromofluorescein free acid in dry powder form or an aqueous dispersion thereof.

19. A composition according to claim 14 containing fluorescein free acid in dry powder form or an aqueous dispersion thereof.

20. A composition according to claim 15 containing at 1:1 mixture of fluorescein:erythrosin B free acids in dry powder form or an aqueous dispersion thereof.

21. A composition according to claim 15 containing a 1:1 mixture of fluorescein:rose bengal free acids in dry powder form or an aqueous dispersion thereof.

22. A composition according to claim 14 for combatting adult insects or insect larvae of the family Culicadae.

23. A composition according to claim 15 for combatting adult insects or insect larvae of the family Culicidae.

* * * * *